United States Patent

Ashline

[11] Patent Number: 5,925,007
[45] Date of Patent: Jul. 20, 1999

[54] CARPAL CUFF

[76] Inventor: Clifford E. Ashline, 5615 Crowley Blvd., Midland, Tex. 79707

[21] Appl. No.: 08/944,470

[22] Filed: Oct. 6, 1997

[51] Int. Cl.[6] ........................................................ A61F 5/00
[52] U.S. Cl. ............................. 602/21; 128/878; 400/715
[58] Field of Search ................................. 602/16, 20, 21, 602/23; 128/870, 877, 878, 879, 881; 400/715; 5/620, 623, 646–647

[56] References Cited

U.S. PATENT DOCUMENTS

| | | | |
|---|---|---|---|
| 4,945,925 | 8/1990 | Garcia ...................................... | 128/877 |
| 4,996,977 | 3/1991 | Tiedeken .................................... | 602/20 |
| 5,136,743 | 8/1992 | Pirela-cruz .......................... | 128/878 X |
| 5,291,903 | 3/1994 | Reeves ..................................... | 128/878 |
| 5,327,912 | 7/1994 | Mally ....................................... | 128/878 |
| 5,348,408 | 9/1994 | Gelardi et al. ............................ | 400/715 |
| 5,702,355 | 12/1997 | Repice et al. .............................. | 602/21 |
| 5,718,671 | 2/1998 | Bzoch ....................................... | 602/20 |
| 5,730,711 | 3/1998 | Kendall et al. ........................ | 602/21 X |

OTHER PUBLICATIONS

Copies of Magazine Advertizements, Jul. '97 Entitled "CTS" and "Wrist Wrap–Up".

*Primary Examiner*—Linda C. M. Dvorak
*Attorney, Agent, or Firm*—Robert N. Blackmon

[57] ABSTRACT

A carpal cuff having a lower bearing surface adapted to be worn on the forearm of a user to prevent repetitive stress injury during the operation of a computer mouse or keyboard. A padded arm support is made of a platform and a cap plate. The platform and cap plate secure a pair of arm straps therebetween and support a pair of rotatably attached bearing spreader plates. The bearing spreader plates each having acrylic bearing attached to which can be spread out from the arm support to a deployed position or stored beneath the arm support by rotating the position of the bearing support plates. When the carpal cuff is attached through the use of the arm straps to the user, the forearm of the user is fixed in a correct and neutral position to transfer weighting of the elbows to the carpal cuff to prevent stress of the wrist and carpal tunnel of the user. The use of the bearing plates allow the user to move the computer mouse without having to lift his arm and the carpal cuff. The use of hook and loop attached straps allow the device to easily be fitted to any user and reduce the likelihood of interference with the circulation or comfort of the user.

11 Claims, 4 Drawing Sheets

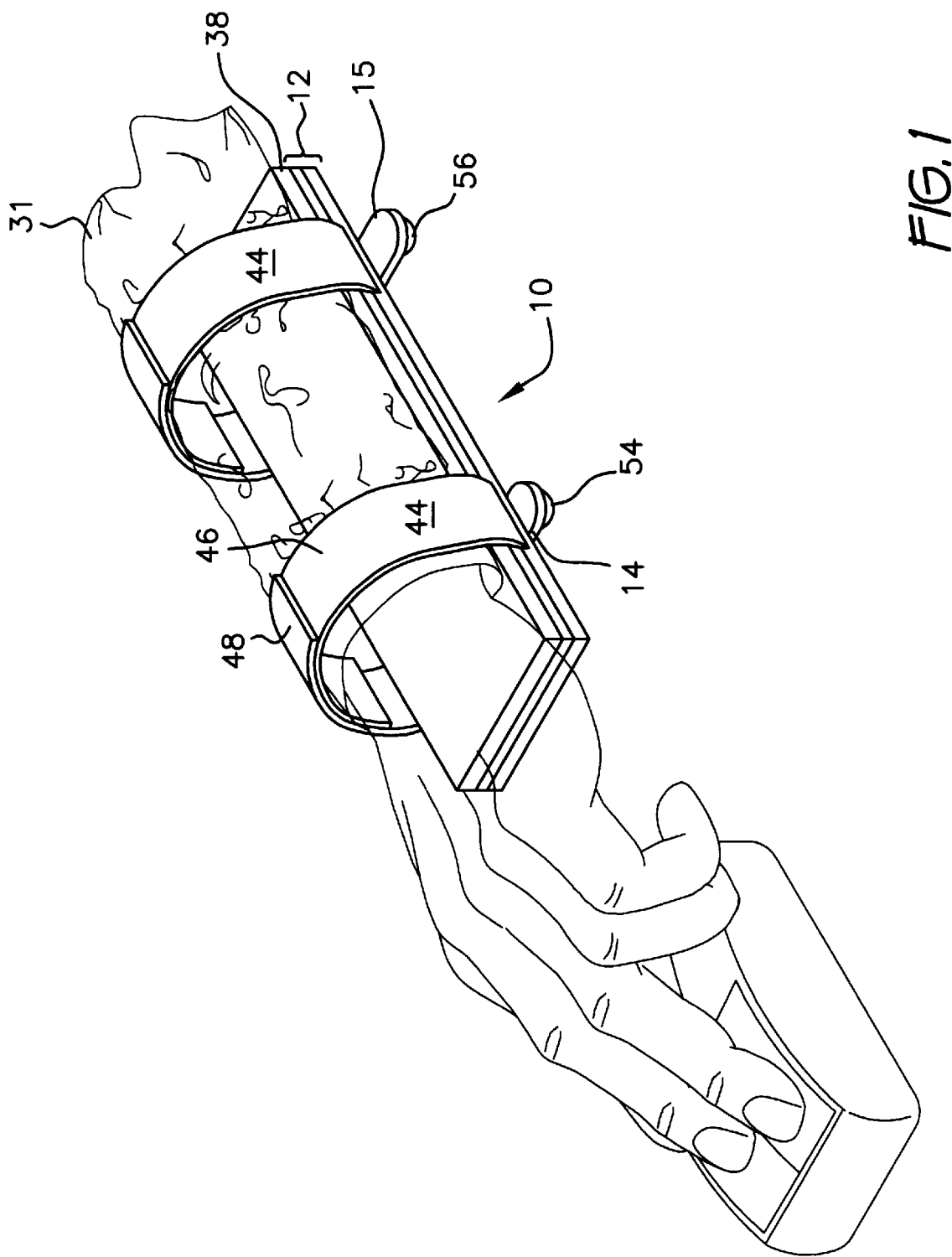

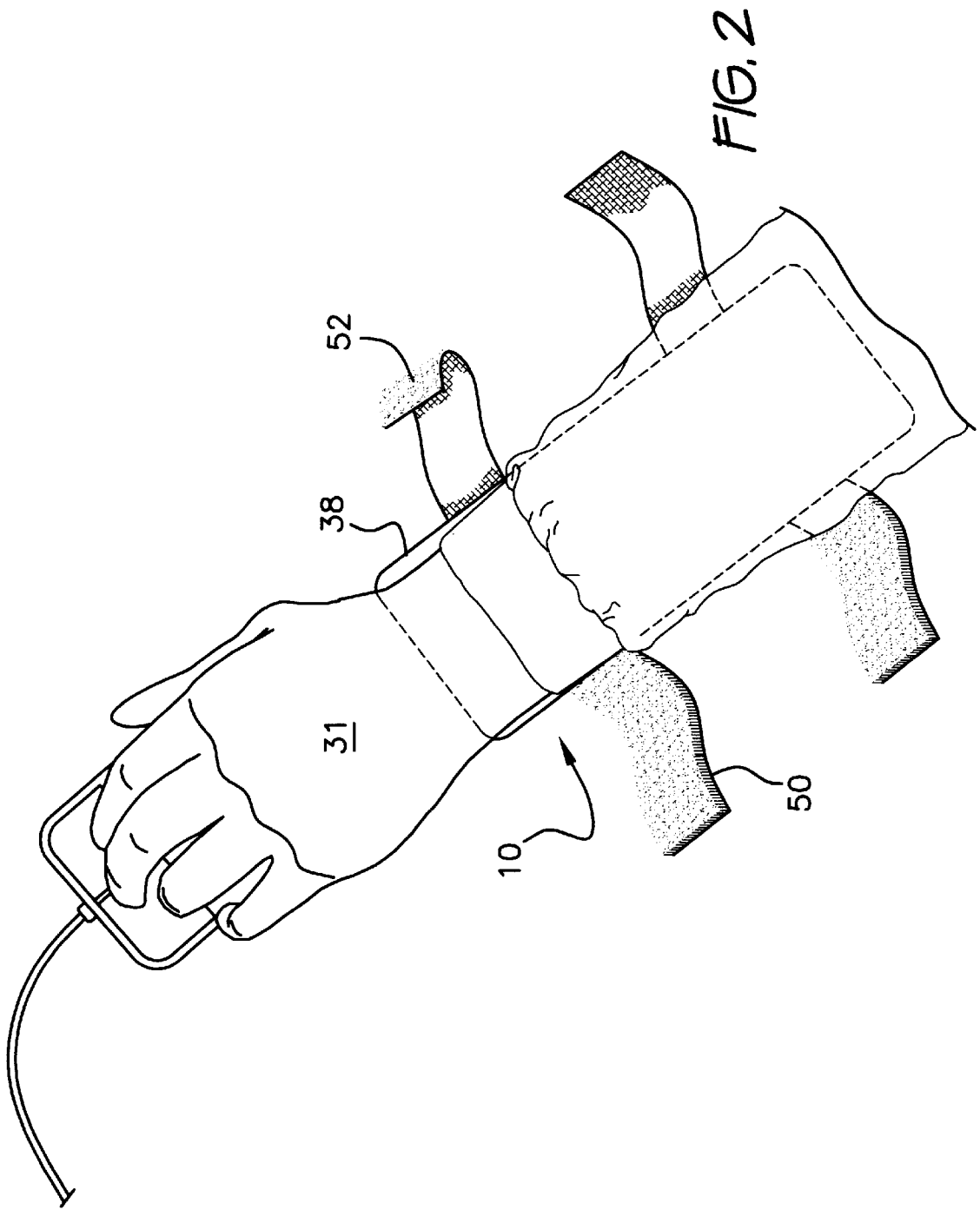

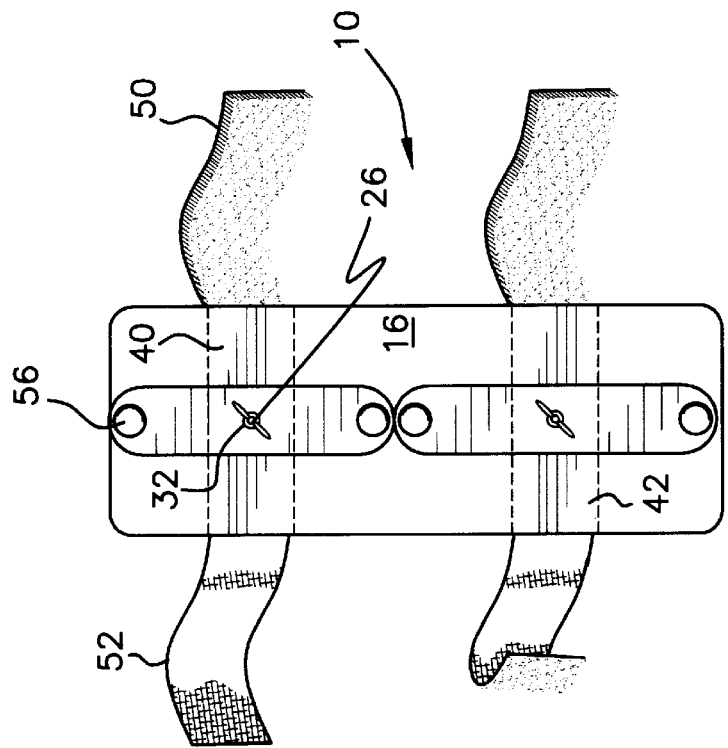
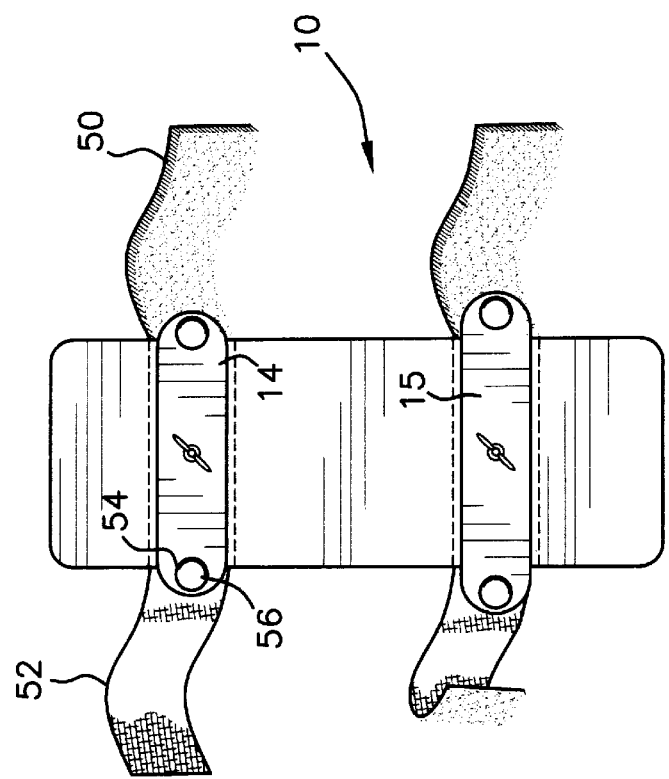

CARPAL CUFF

BACKGROUND OF THE INVENTION

1. Field of the Invention

The present invention relates to a carpal cuff for the prevention and alleviation of Carpal Tunnel Syndrome.

2. Description of the Prior Art

One of the biggest increases in employee downtime in the 1990s has been caused by Carpal Tunnel Syndrome (CTS) which is also called Repetitive Stress Injury (RSI). The Carpal Tunnel is the passageway that leads from the forearm through the wrist. This area can become constricted by inflammation of the tendons or ligaments caused by repetitive or unnatural motion of the hands, wrists, and elbows. These repetitive motions can also cause swelling of the lining of the tunnel resulting is a similar constriction. Stresses to the area can also be caused by a misalignment of the carpal bones in the hand with the elbow joint exacerbating the strain on the carpal tunnel.

The restriction of the Carpal Tunnel can cause several aggravating or debilitating effects on the sufferer. A weakening of the hand strength and the thumb and fingers can result from the Carpal Tunnel Syndrome as well as numbness or soreness or a sense of swelling of the wrist. Persistence of the stress to the Carpal Tunnel can result in the inability of the sufferer to carry out even simple work related tasks causing expensive employee down time. The employee may even be forced to seek medical attention, surgery, or retraining before work can be resumed. Examined on a national scale, CTS can affect millions of workers across all skill levels resulting in billions of dollars in costs to individuals, employers, insurance companies, and health care providers.

Several steps have been taken in the past to alleviate the stress on the wrists to curb Repetitive Stress Disorder. The most common method is the wrist glove or brace as shown in FIG. 6 which is used to provide some support to the thumb and wrist area to persons already suffering from CTS. The devices do not however prevent Carpal Tunnel Syndrome. To go beyond post-CTS support, one must support the area between the wrist and the elbow to effectively prevent the user from injuring the carpal tunnel.

None of the above inventions, taken either singly or in combination, is seen to describe the instant invention as claimed.

SUMMARY OF THE INVENTION

Accordingly, it is a principal object of the invention to provide a carpal cuff which isolates the lower arm as a single unit to prevent stress on the carpal tunnel.

It is another object of the invention to provide a carpal cuff having a padded platform and hook and loop straps to receive the forearm of a user to maintain the elbow, wrist and hand of the user at a neutral level while not interfering with circulation or causing discomfort due to binding or heat build up in the forearm.

It is a further object of the invention to provide a carpal cuff having bearing surfaces which allow the cuff to move along a work surface to perform work while maintaining the lower arm of the user as a unit to prevent stress on the carpal tunnel.

Still another object of the invention is to provide a carpal cuff having extendible bearing spreaders which can be extended to provide a low friction, leveling support for a user's forearm while the user performs ordinary tasks especially along a horizontal surface.

A further object of the invention is to provide a carpal, cuff having retractable bearing supports that can be retracted to make the cuff easily portable or storable.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIG. 1 is an environmental perspective view of a carpal cuff according to the present invention which is shown affixed to a user by a plurality of straps and operated in conjunction with a computer mouse.

FIG. 2 is a top environmental view which shows the hook and loop straps undone so that the device may be removed or affixed to the user. The platform of the cuff is shown in ghost lines to show the relation of the platform to the arm of the user.

FIG. 3 is a bottom plan view of the carpal cuff according to the present invention showing the bearing spreaders and bearings in a deployed position.

FIG. 4 is a bottom plan view of the carpal cuff according to the present invention showing the bearing spreaders and bearings in a retracted position.

Similar reference characters denote corresponding features, consistently throughout the attached drawings.

DETAILED DESCRIPTION OF THE PREFERRED EMBODIMENT(S)

Figure 5:
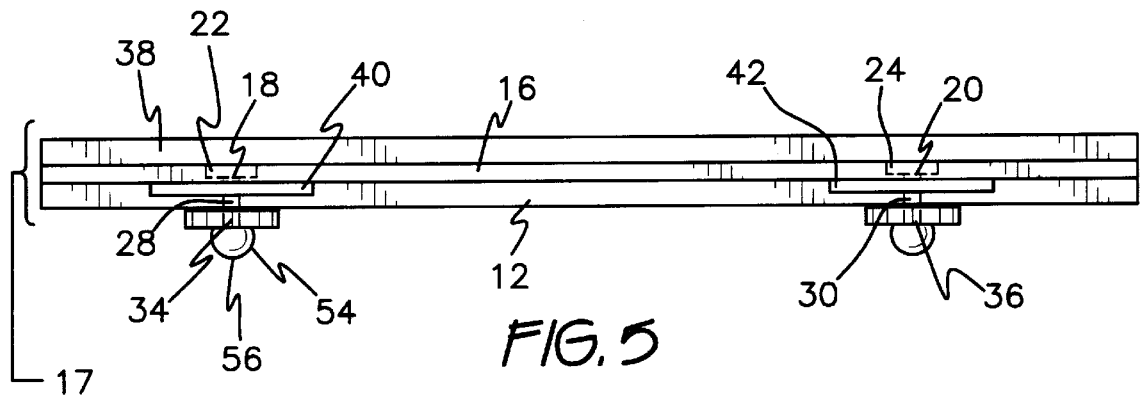
FIG. 5 is a side elevation showing the arm support plate and pad with the straps removed to show channel details.
Figure 6:
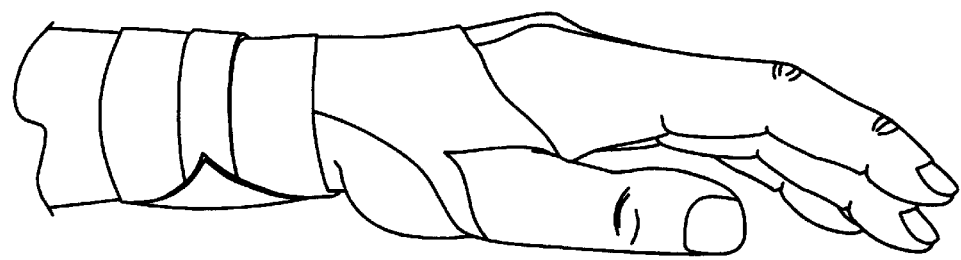
FIG. 6 shows a prior art wrist brace.

Generally referring to FIGS. 1 and 2, there is shown a carpal cuff 10 according to the present invention which can be worn by a user to prevent stress to the carpal tunnel area of the user's forearm 31. The carpal cuff 10 has a central platform 12 which is mounted between two bearing spreader plates 14,15 and a cap 16. The platform can be made from an acrylic base or any other material which provides a suitably stiff base for the carpal cuff. The cap 16 has drill holes 18,20 (FIG. 5) each having a countersunk recessed portion 22,24 for receiving the head of a bolt 26. The central platform 12 also has two through holes 28,30 aligned and equal in diameter to the drill holes 18,20 of the cap plate 16. Each bearing spreader plate has a pair of bearings 54 providing a lower bearing surface 56 and has a central hole 34,36 midway between the two bearing members 54 forming a bearing assembly 57. Each central hole 34,36 is equal in diameter to the drill holes 18,20 and the through holes 28,30.

As best shown in FIG. 3–5, during assembly, the cap plate drill holes 18,20 and platform through holes 28,30 are aligned and a bolt 26 is inserted through each drill hole 18,20 such that the head of the bolt rests within the countersunk recess 22,24 (shown in hidden lines in FIG. 5) of the cap plate. The body of each bolt passes through a respective drill hole of the cap plate 16 and is inserted through a respective through hole 28,30 of the platform 12 to secure the cap plate and the platform together to form an arm support 17. A front bearing spreader plate 14 is mounted to the carpal cuff by inserting one of the bolts through the central hole 34 of the front bearing spreader plate 15. The rear bearing spreader plate 15 is mounted to the carpal cuff by inserting the other bolt through the central hole 36 of the rear bearing spreader plate 15. Each bolt is then held in place and tensioned by threading a wing nut 32 onto the bolt to affix the platform between the bearing spreader plates 14,15 and the cap 16.

An arm pad 38 or an arm/wrist pad is attached on top of the cap plate by adhesive or any other similar method which would be obvious to one of ordinary skill in the art including, but not limited to staples, screws, nails, or clamps. Adhesive is the preferred method as it does not interfere with the smooth upper surface of the pad which contacts the user. The arm pad is preferably perforated to allow air to flow through the pad to prevent undue heat build up between the user and the arm pad.

The carpal cuff has retention means including two arm straps 44 for retaining the carpal cuff on the forearm of the user. The two arm straps 44 are secured between the cap plate and the platform. Two recessed areas on the platform's upper surface form channels 40,42 between the lower surface of the cap plate and the upper surface of the platform when the platform 12 and the cap plate 16 are secured together to form the arm support 17. The straps and channels may be aligned with the bolts 26 such that the straps are held in place and anchored by the passage of the bolts through the cap plate 16, channels 40,42, and platform 12 as described above.

Each strap 44 has a securing means comprising a first end 46 having hook or loop type fasteners 50. Each strap further has a second end 48 having the complimentary hook or loop fastener 52 such that the ends 46,48 of each strap 44 may be secured together to secure around the forearm 31 of a user as shown in FIG. 1.

As best shown in FIGS. 3 and 4, each bearing spreader plate 14,15 consists of an elongated plate having a length preferably greater than the width of the platform 12. By positioning the bearing surfaces 56 at a position below the outer perimeter of the platform or beyond, maximum stability of the carpal cuff can be achieved. The elongated bearing plates 14,15 provide a wider footprint for the carpal cuff so that the device is less likely to tip in one direction or the other. The rear bearing spreader plate 15 which will be closer to the user's elbow is preferably longer than the front bearing spreader plate to enhance the overall stability of the device.

Each of the spreader plates 14,15 is secured to the lower surface of the platform 12 by a central bolt 26 such that each bearing plate may rotate about the bolt. The tension of the wing nut holding the bearing spreader plates against the lower surface of the platform 12 is selected such that the bearing spreader plates will only rotate upon application of a predetermined force by the user, but will normally be held in place by the friction created by the tensioned wing nut and bolt. The bearing plates which are the shape of an elongated bar may be rotated about the bolt to a first, stored position or folded position wherein the longitudinal axis of each bearing spreader plate 14,15 is parallel to the longitudinal axis of the platform for easy storage or portability. The bearing plates may also be rotated to a second, deployed position wherein the longitudinal axis of the bearing spreader plates 14,15 are perpendicular to the longitudinal axis of the platform 12 as described above.

To enhance operation of the spreader plates during rotation from the stored position to the deployed position and back, the length of the spreader plates should be chosen such that they do not interfere with each other. If one half of the length of the front bearing spreader plate 14 and one half of the length of the rear bearing spreader plate 15 is less than the length between the centers of the two through holes 28,30 on the platform then the two bearing spreader plates will not be able to strike each other during rotation of the bearing spreader plates. The length of the bearing spreader plates are thus preferably made as long as possible to enhance the stability of the plates while not interfering with each other so that they can be properly rotated and stored underneath the platform when not in use.

In operation, the carpal cuff is normally stored with the bearing spreader plates aligned with the platform in its stored position to provide as compact a device as possible. This allows the device to be carried in a pocket book, handbag, or briefcase taking up as little room as possible. When a user is ready to type or use a computer mouse or similar activity, the user must attach the device to his forearm to neutralize his forearm to protect his carpal tunnel area.

To secure the device to the user, the user separates the ends 46,48 of the straps 44 from each other by pulling apart the cooperating hook and loop fasteners 50,52. The user then rests his forearm against the perforated arm pad 38 as shown in FIG. 2 and reapplies the hook and loop fasteners 50,52 to secure the straps about the forearm. The use of hook and loop fastened straps provide adjustability of the device to accommodate a wide range of users without interfering with the normal circulation of the user. Devices which use more material can cause reduced circulation in the hand and wrist area and can cause undue generation of heat in the lower arm, causing perspiration or discomfort. The use of the soft perforated arm pad 38 further prevents heat build-up in the area compared to normal wrapped, bandage type devices and provides for maximum comfort.

The user must then deploy the bearings 54 to their operational position by rotating the bearing spreader plates 14,15 from their stored or folded position to their deployed position. The bearing spreader plates may be deployed by rotating the plates such that the bearings 54 which are all stored beneath the plate outward so that the edges of the bearing spreader plates are visible and extended beyond the periphery of the platform as shown in FIG. 3. For best results, the bearing spreader plates should be parallel to each other and perpendicular to the longitudinal axis of the platform. This allows for the maximum stability of the device and reduces the overall friction of the carpal cuff, which is especially important when the hand, wrist and elbow are moved in conjunction with a computer mouse. The bearings are preferably formed from acrylic and are non-rotatingly affixed to the bearing spreader plates, however, one skilled in the art would recognize that ball bearings or other equivalent means could be used in place of the static acrylic bearings.

When the carpal cuff is thus secured to the user as shown in FIG. 1, the wrist, forearm, and elbow are properly aligned. The weight of the user is transferred from the elbow to the carpal cuff. This is especially important when the user has relaxed into a shoulder's rolled forward slouch common among computer users after extended period in front of a computer. This position, which would normally apply greater destructive force to the elbows and wrists of the user, are transferred by the carpal cuff away from the carpal tunnel area and elbows to the cuff. The carpal cuff also further protects the user by keeping the elbow, wrist and hand at the same neutral level to prevent misalignment of the elbow, wrist and hand during operation of a keyboard or mouse.

To remove the carpal cuff, the ends 46,48 of the straps 44 are pulled away from each other releasing the hook and loop fasteners, and the user's arm is lifted off the arm pad 38. The bearing spreader plates 14,15 can then be rotated back underneath the platform for easy storage.

Obviously one skilled in the art would appreciate that the length, height, and shape of the device can easily be modified for particular users or classes of users without departing from the scope of the claims. It is thus to be understood that the present invention is not limited to the sole embodiment described above, but encompasses any and all embodiments within the scope of the following claims.

I claim:

1. A carpal cuff for the prevention of repetitive stress injury comprising:
   a cap plate having an upper and lower surface;
   an arm pad attached to said upper portion of said cap plate for receiving the forearm of a user;
   a platform having an upper surface attached to said lower surface of said cap plate and having a lower surface;
   an elongated front bearing spreader plate rotatably attached to said lower surface of said platform and having first and second ends; said front bearing spreader plate being rotatable between a front bearing spreader plate stored position and a front bearing spreader plate deployed position;
   said front bearing spreader plate first and second ends each having a bearing mounted therein;
   an elongated rear bearing spreader plate rotatably attached to said lower surface of said platform and spaced apart from said front bearing spreader plate and having first and second ends; said rear bearing spreader plate being rotatable between a rear bearing spreader plate stored position and a rear bearing spreader plate deployed position;
   said rear bearing spreader plate first and second ends each having a bearing mounted therein;
   a first and second strap secured between said cap plate and said platform;
   said first strap having a first and second end having cooperating hook and loop fasteners for securing said first strap about the forearm of the user;
   said second strap having a first and second end having cooperating hook and loop fasteners for securing said second strap about the forearm of the user;
   whereby the forearm of the user is secured to the carpal cuff by said first and second straps such that the wrist, arm and elbow of the user are held in a neutral position to lower the stresses on the forearm of the user.

2. A carpal cuff for the prevention of repetitive stress injury to the arm of a user comprising:
   an arm support plate having a lower surface;
   a bearing assembly attached to said lower surface of said arm support plate;
   retention means for securing the forearm of the user to the arm support plate whereby the forearm of the user is fixedly retained against the arm support plate to reduce the stress on the elbow, wrist, and hand of the user;
   said bearing assembly includes at least one bearing spreader plate rotatably attached to said lower surface of said platform;
   said at least one bearing spreader having a first and second end and wherein each said first and second ends has a bearing affixed thereto whereby frictional engagement of said carpal cuff with a working surface is reduced.

3. A carpal cuff according to claim 2 wherein said bearing is an acrylic ball non-rotatably attached to said at least one bearing spreader.

4. A carpal cuff for the prevention of repetitive stress injury to the arm of a user comprising:
   an arm support plate having a lower surface;
   a bearing assembly attached to said lower surface of said arm support plate; and
   retention means for securing the forearm of the user to the arm support plate;
   whereby the forearm of the user is fixedly retained against the arm support plate to reduce the stress on the elbow, wrist, and hand of the user;
   said bearing assembly including an elongated front bearing spreader plate rotatably attached to said lower surface of said platform and having first and second ends; said front bearing spreader plate being rotatable between a front bearing spreader plate stored position and a front bearing spreader plate deployed position;
   said front bearing spreader plate first and second ends each having a bearing mounted therein;
   an elongated rear bearing spreader plate rotatably attached to said lower surface of said platform and spaced apart a predetermined distance from said front bearing spreader plate and having first and second ends; said rear bearing spreader plate being rotatable between a rear bearing spreader plate stored position and a rear bearing spreader plate deployed position;
   said rear bearing spreader plate first and second ends each having a bearing mounted therein;
   whereby said front and rear bearing spreader plates may be rotated from a stored position for storage of the carpal cuff to a deployed position for deployment of the carpal cuff.

5. A carpal cuff according to claim 4 wherein said front bearing spreader plate is an elongated bar having a first longitudinal length and said rear bearing spreader plate is an elongated bar having a second longitudinal length;
   said arm support plate having a width and a length; and
   wherein said second longitudinal length of said rear bearing spreader plate is at least as great as said width of said support plate.

6. A carpal cuff according to claim 5 wherein said rear bearing spreader plate second longitudinal length is greater than the width of said support plate.

7. A carpal cuff according to claim 6 wherein said front bearing plate first longitudinal length is at least as long as said width of said support plate.

8. A carpal cuff for the prevention of repetitive stress injury to the arm of a user comprising:
   an arm support plate having a lower surface;
   a bearing assembly attached to said lower surface of said arm support plate;
   retention means for securing the forearm of the user to the arm support plate whereby the forearm of the user is fixedly retained against the arm support plate to reduce the stress on the elbow, wrist, and hand of the user,
   said arm support plate including a platform and a cap plate;
   said cap plate having an upper and lower surface;
   an arm pad attached to said upper portion of said cap plate for receiving the forearm of a user;
   said platform having an upper surface attached to said lower surface of said cap plate and having a lower surface for receiving said bearing assembly;
   said bearing assembly including at least one bearing spreader plate rotatably attached to said lower surface of said platform and said at least one bearing spreader plate has at least one bearing attached whereby frictional engagement of said carpal cuff with a working surface is reduced; and wherein said at least one bearing spreader has a first and second end and wherein each said first and second ends has a bearing affixed thereto and said bearing is an acrylic ball non-rotatably attached to said at least one bearing spreader.

9. A carpal cuff for the prevention of repetitive stress injury to the arm of a user comprising:

an arm support plate having a lower surface;

a bearing assembly attached to said lower surface of said arm support plate;

retention means for securing the forearm of the user to the arm support plate whereby the forearm of the user is fixedly retained against the arm support plate to reduce the stress on the elbow, wrist, and hand of the user, said arm support plate including a platform and a cap plate;

said cap plate having an upper and lower surface;

an arm pad attached to said upper portion of said cap plate for receiving the forearm of a user;

said platform having an upper surface attached to said lower surface of said cap plate and having a lower surface for receiving said bearing assembly;

said bearing assembly including an elongated front bearing spreader plate rotatably attached to said lower surface of said platform and having first and second ends;

said front bearing spreader plate being rotatable between a front bearing spreader plate stored position and a front bearing spreader plate deployed position;

said front bearing spreader plate first and second ends each having a bearing mounted therein;

an elongated rear bearing spreader plate rotatably attached to said lower surface of said platform and spaced apart a predetermined distance from said front bearing spreader plate and having first and second ends; said rear bearing spreader plate being rotatable between a rear bearing spreader plate stored position and a rear bearing spreader plate deployed position; and said rear bearing spreader plate first and second ends each having a bearing mounted therein;

whereby said front and rear bearing spreader plates may be rotated from a stored position for storage of the carpal cuff to a deployed position for deployment of the carpal cuff.

10. A carpal cuff for the prevention of repetitive stress injury to the arm of a user comprising:

an arm support plate having a lower surface;

a bearing assembly attached to said lower surface of said arm support plate; and retention means for securing the forearm of the user to the arm support plate;

whereby the forearm of the user is fixedly retained against the arm support plate to reduce the stress on the elbow, wrist, and hand of the user;

said bearing assembly including an elongated front bearing spreader plate rotatably attached to said lower surface of said platform and having first and second ends;

said front bearing spreader plate being rotatable between a front bearing spreader plate stored position and a front bearing spreader plate deployed position;

said front bearing spreader plate first and second ends each having a bearing mounted therein;

an elongated rear bearing spreader plate rotatably attached to said lower surface of said platform and spaced apart a predetermined distance from said front bearing spreader plate and having first and second ends; said rear bearing spreader plate being rotatable between a rear bearing spreader plate stored position and a rear bearing spreader plate deployed position; and said rear bearing spreader plate first and second ends each having a bearing mounted therein;

whereby said front and read bearing spreader plates may be rotated from a stored position for storage of the carpal cuff to a deployed position for deployment of the carpal cuff.

11. A carpal cuff according to claim 10 wherein said front bearing spreader plate is an elongated bar having a first longitudinal length and said rear bearing spreader plate is an elongated bar having a second longitudinal length;

said arm support plate having a width and a length; wherein said second longitudinal length of said rear bearing spreader plate at least as long as said width of said arm support plate and further wherein said front bearing spreader bearing plate first longitudinal length is at least as long as said width of said arm support plate.

* * * * *